(12) United States Patent
Li et al.

(10) Patent No.: US 7,569,545 B2
(45) Date of Patent: *Aug. 4, 2009

(54) METHODS OF INCREASING NEUROTROPHIC FACTOR EXPRESSION

(75) Inventors: Hung Li, Taipei (TW); Woei-Cherng Shyu, Taipei (TW); Shinn-Zong Lin, Hualien (TW)

(73) Assignee: Academia Sinica, Taipei (TW)

(*) Notice: Subject to any disclaimer, the term of this patent is extended or adjusted under 35 U.S.C. 154(b) by 440 days.

This patent is subject to a terminal disclaimer.

(21) Appl. No.: 11/134,613

(22) Filed: May 20, 2005

(65) Prior Publication Data

US 2006/0263332 A1   Nov. 23, 2006

(51) Int. Cl.
*A61K 38/18* (2006.01)
*G01N 33/53* (2006.01)

(52) U.S. Cl. .......................................... 514/12; 435/7.1

(58) Field of Classification Search .................. None
See application file for complete search history.

(56) References Cited

U.S. PATENT DOCUMENTS

| | | | |
|---|---|---|---|
| 6,749,850 B1 * | 6/2004 | Finkelstein et al. | 424/93.7 |
| 6,761,888 B1 * | 7/2004 | Schenk | 424/130.1 |
| 2004/0019184 A1 * | 1/2004 | Fukuda et al. | 530/350 |
| 2004/0120925 A1 * | 6/2004 | Toda et al. | 424/85.2 |
| 2004/0265971 A1 | 12/2004 | Sato et al. | |

FOREIGN PATENT DOCUMENTS

WO          00/50568    *   8/2000

OTHER PUBLICATIONS

Definition of Neurotrophic Factor, Medline Plus online dictionary, accessed Mar. 24, 2008.*
Zhao 2002 (Experimental Neurology 174:11-20).*
Schabitz et al. 2003. Stroke 34:745-751.*
Modo 2004 (NeuroImage 21:311-317).*
Borlongan, Cesar V. and David C. Hess, "G-CSF-Mobilized Peripheral Blood from Transplantation Therapy in Stroke," *Cell Transplantation*, 12:447-448 (2003).
Cao et al., "Stem Cell Repair of Central Nervous System Injury," *Journal of Neuroscience Research*, 68:501-510 (2002).
Corti et al., "Modulated Generation of Neuronal Cells from Bone Marrow by Expansion and Mobilization of Circulating Stem Cells with In Vivo Cytokine Treatment," *Experimental Neurology*, 177:443-452 (2002).
Gerstring et al., "Effects of Enterally Administering Granulocyte Colony-Stimulating Factor to Suckling Mice," *Pediatric Research*, 55(5):802-806 (2004).
Maianski et al., "Bid Truncation, Bid/Bax Targeting to the Mitochondria, and Caspase Activation Associated with Neutrophil Apoptosis are Inhibited by Granulocyte Colony-Stimulating Factor," *The Journal of Immunology*, 172:7024-7030 (2004).
Ricciardi et al., "Apoptosis Susceptibility and Cell-Cycle Distribution in Cells from Myelodysplastic Syndrome Patients: Modulatory In-Vitro Effects of G-CSF and Interferon-α," *Leukemia & Lymphoma*, 45(7):1437-1443 (2004).
Rudolf et al., "Clozapine-induced Agranulocytosis and Thrombopenia in a Patient with Dopaminergic Psychosis," *J. Neural. Transm.* 104:1305-1311 (1997).
Savitz et al., "Cell Transplants Offer Promise for Stroke Recovery," *The Journal of Cardiovascular Nursing*, 18(1):57-61 (2003).
Schäbitz et al., "Neuroprotective Effect of Granulocyte Colony-Stimulating Factor After Focal Cerebral Ischemia," *Stroke*, 34:745-751 (2003).
Six et al., "Beneficial Effect of Pharmacological Mobilization of Bone Marrow in Experimental Cerebral Ischemia," *European Journal of Pharmacology*, 458:327-382 (2003).
Willing et al. "Mobilized Peripheral Blood Cells Administered Intravenously Produce Functional Recovery in Stroke," *Cell Transplantation*, 12:449-454 (2003).

* cited by examiner

*Primary Examiner*—Daniel E. Kolker
(74) *Attorney, Agent, or Firm*—Occhiuti Rohlicek & Tsao LLP

(57) ABSTRACT

Methods of treating brain tissue damage and increasing expression of a trophic factor in a cell.

7 Claims, No Drawings

METHODS OF INCREASING NEUROTROPHIC FACTOR EXPRESSION

BACKGROUND

Brain tissue damages, resulting either from injuries or disorders (e.g., neurodegenerative and cerebrovascular diseases, are a leading cause of long-term disability. Due to their pluripotency, embryonic stem cells (ES cells) hold a great promise for treating brain tissue damage (Lindvall et al., 2004, Nat. Med., 10 Suppl:S42-50; and Taguchi et al., 2004, J. Clin. Invest.; 114(3):330-338). However, ethical and logistical considerations have hampered their use (Barinaga, 2000, Science, 287(5457):1421-1422; and Boer, 1994, J. Neurol., 242 (1):1-13). Use of non-ES pluripotent cells has also been exploited. They include adult bone marrow mesenchymal stem cells (MS cells) or stromal cells (Sanchez-Ramos et al., 2000, Exp. Neurol., 164(2):247-256 and Woodbury et al., 2000, J. Neurosci. Res., 61(4):364-370) and umbilical cord blood cells (UCB cells) (Galvin-Parton et al., 2003, Pediatr. Transplant. 2003; 7(2):83-85 and Ha et al., 2001 Neuroreport., 2(16):3523-3527). Nonetheless, requirements for in vitro expansion and HLA-matching have limited clinical applications of these cells as well. Thus, there is a need for alternatives to MS cells and UCB cells.

SUMMARY

This invention is based, at least in part, on the discovery that brain tissue damage can be repaired by administration of granulocyte-colony stimulating factor (G-CSF) and transplantation of mobilized peripheral blood hematopoietic stem cells (PBSCs).

Accordingly, one aspect of this invention features a method of treating brain tissue damage. The method includes identifying a subject suffering from or being at risk for developing brain tissue damage, and administering to the subject an effective amount of a G-CSF and an effective amount of PBSCs. The PBSCs are administered intracerebrally. Preferably, the PBSCs are autologous to the subject. For example, the cells are enriched from the subject after the subject is administered G-CSF. In one embodiment, G-CSF is administered subcutaneously. It can be administer at 10 to 200 μg/day/kg body weight for 2-10 days; preferably, 20 to 100 μg/day/kg body weight for 3-8 day; and, more preferably about 50 μg/day/kg body weight for 5 days. The PBSC can administered at $1 \times 10^4$ to $1 \times 10^6$/administration; preferably $5 \times 10^4$ to $8 \times 10^6$/administration; and, more preferably $1 \times 10^5$ to $6 \times 10^5$/administration. The method can be used to treat brain tissue damage caused by a cerebral ischemia, e.g., stroke, or a neurodegenerative disease, e.g., Parkinson's disease, Alzheimer's disease, Spinocerebellar disease, or Huntington's disease.

Treating" refers to administration of a compound or composition (e.g., a cell composition) to a subject, who is suffering from or is at risk for developing brain tissue damage or a disorder causing such damage, with the purpose to alleviate, relieve, remedy, or ameliorate the damage/disorder, the symptom of the damage/disorder, the disease state secondary to the damage/disorder, or the predisposition toward the damage/disorder. An "effective amount" refers to an amount of the compound or composition that is capable of producing a medically desirable result, e.g., as described above, in a treated subject. The treatment method can be performed alone or in conjunction with other drugs or therapies.

This invention also features a method of increasing the expression level of a neurotrophic factor in a cell, e.g., a brain cell in a subject in need thereof, by contacting the cell with G-CSF. Examples of the neurotrophic factor include Brain-Derived Neurotrophic Factor (BDNF), Glial-cell line Derived Neurotrophic Factor (GDNF), Nerve Growth Factor (NGF), or Stromal Cell Derived Factor-1 (SDF-1). When using this method to treat a subject suffering from or being at risk for developing brain tissue damage, one can measure an expression level of the neurotrophic factor in a sample obtained from the subject before or after administration of G-CSF to confirm an increase in expression.

The details of one or more embodiments of the invention are set forth in the description below. Other features, objects, and advantages of the invention will be apparent from the description and from the claims.

DETAILED DESCRIPTION

The present invention relates to using PBSCs in treating brain tissue damage. Like ES cells, MS cells, and UCB cells, PBSCs possess potential to differentiate into various cells, including neuronal cells or glial cells. PBSCs therefore can be used, together with G-CSF, to regenerate the cells and thereby treat brain tissue damage. Due to fewer restrictions, PBSCs represent a promising alternative to other pluripotent cells. However, the number of PBSCs under a steady-state condition is very low. In a preferred embodiment of this invention, PBSCs used for treating brain tissue damage are obtained as follows. They are first enriched by administration of G-CSF to mobilize hematopoietic stem cells (HSCs) from bone marrow into the peripheral blood, and then purified from the blood.

Within the scope of this invention is a method of treating brain tissue damage in a subject. The method includes identifying a subject suffering from or being at risk for developing a brain tissue damage. The subject can be a human or a non-human animal, such as a cat, a dog, or a horse. Examples of the brain tissue damage includes those caused by a cerebral ischemia (e.g., chronic stroke) or a neurodegenerative disease (e.g., Parkinson's disease, Alzheimer's disease, Spinocerebellar disease, or Huntington's disease). A subject to be treated can be identified by standard techniques for diagnosing the conditions or disorders of interest. The treatment method entails administering to the subject an effective amount of G-CSF.

While many G-CSF preparations can be used, highly purified G-CSF is preferred. Examples of G-CSF include mammalian G-CSF (e.g., human G-CSF, or G-CSF having substantially the same biological activity as mammalian G-CSF. Both naturally occurring and genetic engineered G-CSF can be used. G-CSF obtained by genetic engineering may be that having the same amino acid sequence as naturally occurring G-CSF or an functionally equivalent there of. A "functional equivalent" refers to a polypeptide derivatives of a naturally occurring G-CSF, e.g., a protein having one or more point mutations, insertions, deletions, truncations, a fusion protein, or a combination thereof. It possesses one or more of the activities of G-CSF, e.g., the ability to mobilize stem cells from bone marrow into the peripheral blood, to increase the expression of one of the trophic factors noted above, or to protect cells from cell death. For reports on G-CSF derivatives, see U.S. Pat. No. 5,581,476; U.S. Pat. No. 5,214,132; U.S. Pat. No. 5,362,853; and U.S. Pat. No. 4,904,584. The term "G-CSF" also covers chemically modified G-CSF. Examples of chemically modified G-CSF include G-CSF subjected to conformational change, addition or deletion of the sugar chain, and G-CSF to which a compound such as polyethylene glycol has been bound (see, e.g., U.S. Pat.

No. 5,824,778; U.S. Pat. No. 5,824,784; WO 96/11953, WO 95/21629, WO 94/20069, U.S. Pat. No. 5,218,092, JP 1992-164098 A). Once purified and tested by standard methods, G-CSF can be administered to a subject for mobilizing and enriching PBSCs as described below. G-CSF is administered at, e.g., 10 to 200 μg/day/kg body weight for 2-10 days, via any suitable routes.

To practice the treatment method of this invention, one can administer G-CSF parenterally. The term "parenteral" as used herein includes intracerebral, subcutaneous, intracutaneous, intravenous, intramuscular, intraarterial, intraperitoneal, intrasternal, intrathecal, and intracranial injection or infusion techniques. Examples of parenteral administration also include delivering via inhalation spray or implantation.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol, or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included and, if desired, agents imparting color or fragrance as well. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water. More specifically, an active ingredient dissolved in a small amount of an oil (e.g., almond oil) is admixed to the mixture. An example of such a cream includes about 40 parts water, about 20 parts beeswax, about 40 parts mineral oil and about 1 part almond oil. Ointments may be formulated by mixing a solution of an active ingredient in a vegetable oil, such as almond oil, with warm soft paraffin and allowing the mixture to cool. An example of such an ointment includes about 30% almond and about 70% white soft paraffin by weight.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active compounds. Examples of other carriers include colloidal silicon dioxide, magnesium stearate, cellulose, sodium lauryl sulfate, and D&C Yellow # 10.

Suitable in vitro assays can be used to preliminarily evaluate the efficacy of an G-CSF preparation. For example, one can measure the level of one of the trophic factors described above or the level of neurite growth in cells. More specifically, a test preparation can be added to a suitable cell culture (e.g., a primary culture of rat or mouse neuron-glial cells as described in Example 2 below) and the level is determined. One then compares the level with a control level obtained in the absence of the preparation. If the level of interest is higher than the control, the preparation is identified as being active for treating brain tissue damage. One can also evaluate the efficacy of an G-CSF preparation by examining the preparation's effects on cell death according to standard methods. For example, one can measure the level of a protein involved in cell-death (e.g., caspase). If the level is lower than that obtained in the absence of the preparation, the preparation is determined to be active.

The preparation can further be examined for its efficacy in mobilizing HSC to the peripheral blood or treating brain tissue damage by an in vivo assay. For example, the preparation can be evaluated in an animal (e.g., a mouse or rat model). The level of mobilized PBSCs in the peripheral blood is determined by standard methods.

The preparation can also be administered to an animal model having brain tissue damage or a disorder causing such damage. The therapeutic effects of the preparation are then accessed according to standard methods (e.g., those described in Examples 1-3 below). To confirm efficacy in promoting cerebrovascular angiogenesis, one can examine the animal before and after the treatment by standard brain imaging techniques, such as computed tomography (CT), Doppler ultrasound imaging (DUI), magnetic resonance imaging (MRI), and proton magnetic resonance spectroscopy ($^1$H-MRS).

One can also measure the expression level of a trophic factor or a cell death-related protein in a sample (e.g., cerebrospinal fluid) obtained from the animal before or after administration of G-CSF to confirm efficacy. The expression level can be determined at either the mRNA level or the protein level. Methods of measuring mRNA levels in a tissue sample or a body fluid are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a tissue sample or a body fluid are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent/luminescent agents (e.g., fluorescein, rhodamine, phycoerythrin, GFP, BFP, and Qdot™ nanoparticles supplied by the Quantum Dot Corporation, Palo Alto, Calif.). Other applicable methods include quantitative immunoprecipitation or complement fixation assays.

Based on the results from the assays described above, an appropriate dosage range and administration route can be determined. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.001-100 mg/kg. Dosage variations are necessary in view of the variety of compounds available and the different efficiencies of various routes of administration. The variations can be adjusted using standard empirical routines for optimization as is well understood in the art.

The treatment method of this invention optionally includes administering to a subject an effective amount of PBSCs. Both heterologous and autologous PBSC can be used. In the former case, HLA-matching should be conducted to avoid or minimize host reactions. In the latter case, autologous PBSCs are enriched and purified from a subject to be treated before the cells are introduced back to the subject. In both cases, G-CSF is used as the active ingredient to mobilize hematopoietic stem cells (HSCs) out of bone marrow so as to increase the number of stem cells in the peripheral blood, which home to the brain (HSCs, once in the peripheral blood, are called peripheral blood stem cells or PBSC). In a preferred embodiment, PBSCs are obtained from a subject as follows: A subject is first administered G-CSF to mobilize HSCs from bone marrow into the peripheral blood. After this enriching step, peripheral blood are collected and PBSCs purified.

To prepare PBSCs, G-CSF is administered at 10 to 200 μg/day/kg body weight for 2-10 days. The G-CSF can be administered to a subject via any suitable routes. Examples include injection subcutaneously, intramuscularly, and intraperitoneally. PBSCs are generally purified based on their physical and biochemical properties. For example, peripheral blood cells may be concentrated for hematopoietic stem cells by centrifugation, counter-current elutriation, selection with cell surface markers (e.g., CD34+ or stem cell related antibodies), or removal of lineage positive (committed) hematopoietic cells. Such methods are well-known in the art. See e.g., U.S. Pat. Nos. 5,061,620; 5,087,570; 5,061,620; 4,714, 680; 4,965,204; and 5,035,994. Example 1 below provides a detail protocol, which routinely results in greater than 90% purity of PBSCs.

Purified PBSCs are tested and stored by standard techniques. They can be administered intracerebrally to a subject in need thereof. In general, $1 \times 10^4$ and $1 \times 10^6$ (e.g., $5 \times 10^4$ to $8 \times 10^6$ and more preferably $1 \times 10^5$ to $6 \times 10^5$) cells are administered. Multiple sites can be used depending on the site and nature of particular damage. Example 1 below describes approximate coordinates for administering cells in a rat stroke model and a Parkinson's disease model. Coordinates for other disorders in other species can be determined accordingly based on comparative anatomy.

Before or after the treatment, a subject can be examined to confirm treatment efficacy. To this end, one can use suitable standard tests or techniques described above and in the examples below.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE 1

G-CSF and mobilized PBSC (MPBSC) transplantation were used in treating brain damage caused by stroke in rat models of brain ischemia.

Thirty adult male Sprague-Dawley rats (weighing 250-300 g) were subjected to three-vessel ligation. All surgical procedures were performed using sterile/aseptic techniques in accordance with University Institutional guidelines. The rats were anesthetized with chloral hydrate (0.4 g/kg) ip. Ligation of the right middle cerebral artery (MCA) and bilateral common carotids (CCAs) were performed by a methods modified from that described in Chen et al. (Stroke, 1986; 17(4):738-743). CCAs were clamped with non-traumatic arterial clips. Under a surgical microscope, a 2×2 mm craniotomy was drilled where the zygoma fuses to the squamosal bone. The right MCA was ligated with an 10-O nylon suture. Cortical blood flow was measured continuously with a laser Doppler flowmeter (PF-5010, Periflux system, Perimed AB, Stockholm, Sweden) in anesthetized animals. A burr hole (1-mm diameter) was made in the right frontoparietal region to allow placement of photodetectors. A probe (0.45 mm in diameter) was stereotaxically placed in the cortex (1.3 mm posterior, 2.8 mm lateral to the bregma, and 1.0 mm below the dura). After 90 minutes of ligation, the suture on the MCA and arterial clips on CCAs were removed to allow reperfusion. The core body temperature was monitored with a thermistor probe and maintained at 37° C. with a heating pad during anesthesia. After each rat recovered, the body temperature was maintained at 37° C. with a heat lamp. As expected, all of the rats developed significant body asymmetry and turned contralateral to the side of the ischemic brain on day 1 following cerebral ischemia. These rats were then treated by G-CSF or the combination of G-CSF and MPBSCs (G-CSF/MPBSC).

To obtain MPBSCs, rats were injected with G-CSF (50 μg/kg) subcutaneously once a day for 5 days. Peripheral blood was collected in sterile tubes containing a citrate-dextrose solution as an anti-coagulant. Mononuclear cells (MNCs) were isolated from umbilical cord blood using the ficoll-Histopaque (Sigma Immunochemicals) centrifugation method (Asahara et al., 1997, Science, 275(5302):964-967). The MNC layer was collected and washed twice with 1 mM EDTA in PBS. $CD^{34+}$ MNCs were separated from $2 \times 10^8$ MNCs by a magnetic bead separation method (MACS; Miltenyi Biotec, Gladbach, Germany). In brief, $CD^{34+}$ MNCs were labeled with a hapten-conjugated mAb against CD34 (BD-pharmingen), followed by an anti-hapten Ab coupled with microbeads. The bead-positive cells ($CD^{34+}$ MNCs) were enriched on positive-selection-columns set in a magnetic field. FACS analysis using anti-CD34 antibodies (BD-pharmingen) labeled with phycoerythrin (PE) (Becton Dickinson) of MACS-sorted cells showed that 91%±3% of the selected cells were positive for CD34. Cells were then labeled with 1

μg/mL bisbenzimide (Hoechst 33342; Sigma, U.S.A.), or 40 μg/ml DiI (Molecular Probe, Eugene), and cultured in RPMI (Gibco, Grand Island, N.Y., USA) plus 10% FBS (Hyclone, Road Logan, Utah) at 37° C. in a humidified atmosphere of 5% $CO_2$/95% air and antibiotics for one hour. These cells were then propagated and stored as aliquots of $1\times10^7$ cells.

The purified cells were then administered to the above-described rat models of cerebral ischemia. More specifically, the above-described 30 rats were divided into three groups (10 in each), i.e., "G-CSF group," "Control group, and "G-CSF/MPBSC group." Seven days later, each rat in the G-CSF group was injected subcutaneously with human recombinant G-CSF (50 μg/kg, Amgen Biologicals), once daily for 5 days. Each rat in the Control group was injected subcutaneously with saline once daily for 5 days. Each rat in the G-CSF-MPBSC group was injected with G-CSF (50 μg/kg) subcutaneously for 5 days. At day 12, bisbenzimide-labeled MPBSCs (approximately $6\times10^5$ cells in 3-5 μl PBS) were transplanted intracerebrally through a 26-gauge Hamilton syringe into 3 cortical areas, 3.0 to 5.0 mm below the dura. The approximate coordinates for these sites were 1.0 to 2.0 mm anterior to the bregma and 3.5 to 4.0 mm lateral to the midline, 0.5 to 1.5 mm posterior to the bregma and 4.0 to 4.5 mm lateral to the midline, and 3.0 to 4.0 mm posterior to the bregma and 4.5 to 5.0 mm lateral to the midline. The needle was retained in place for 5 minutes after each injection and a piece of bone wax was applied to the skull defects to prevent leakage of the injected solution.

To evaluate neurological function in the above-described three groups of rats, behavioral assessments were carried out 3 days before cerebral ischemia, and 1, 7, 14, 21 and 28 days after the treatments noted above. The assessments measured (a) body asymmetry, (b) locomotor activity, and (c) grip strength. The baseline-test scores were recorded in order to normalize those taken after cerebral ischemia.

The elevated body swing test (EBST) was used to assess body asymmetry after MCA ligation and evaluated quantitatively in the manner described in Borlongan et al., 1998, Neuroreport, 9(12):2837-2842. Initially, each rat was examined for lateral movement while its body was suspended by the tail. The frequency of initial head swing contra-lateral to the ischemic side was counted in twenty continuous tests and normalized in the manner described in Chang et al. (Stroke. 2003; 34(2):558-564.)

In locomotor activity tests, each rat was subjected to VersaMax Animal Activity monitoring (Accuscan Instruments, Inc., Columbus, Ohio) for about 2 hours for behavioral recording. The VersaMax Animal Activity monitor contained 16 horizontal and 8 vertical infrared sensors spaced 87 cm apart. The vertical sensors were situated 10 cm from the floor of the chamber. Locomotor activity was counted as the number of beams broken by a rats movement in the chamber. Three vertical parameters defined in the manufacturer's menu option were calculated over 2 hours at night: (i) vertical activity, (ii) vertical time, and (iii) number of vertical movements.

The behavioral measurement scores were all normalized against the baseline scores. It was found that, from 14 to 28 days after treatment, the rats treated with G-CSF/MPBSC exhibited significantly reduced body asymmetry in comparison with the rats in the G-CSF or Control group. Meanwhile, the rats in the G-CSF/MPBSC group showed significantly increases in vertical activity, vertical movement time, and the number of vertical movements in comparison with the rats in the other two groups.

Grip strength was analyzed using a Grip Strength Meter (TSE-Systems, Germany) by a method modified from that described in Stephen (Neurosci. Lett. 1998; 264:1-4). Briefly, grip strength ratio was measured on each forelimb and calculated as the ratio between the mean strength out of 20 pulls of the side contralateral to the ischemia and that of ipsilateral side. In addition, the ratio of grip strength before the treatment ("Pre Tx") and afterwards (day 28; "Post Tx") and baseline were also calculated and changes were present as a percentage of baseline value. It was found that ratios were about 0.6, 0.72, and 1.2 for the rats in the Control, G-CSF, and G-CSF/PBSC groups, respectively. The grip strength results reveal that the rats in the G-CSF/MPBSC group showed higher ratio of grip strength than the rats in the other two groups.

Magnetic Resonance Imaging (MRI) was used to examine the infarcted areas of each rat in the above-described three groups. Each rat was imaged at days 3, 7, 14, and 28 after treatment. MRI was obtained for each rat on a 3.0-Tesla whole-body Signa EchoSpeed MR scanner (General Electric, Milwaukee, Wis.). The rat was anesthetized with chloral hydrate (0.4 g/kg, ip), supported on a wooden cradle, and its head placed in a home-made birdcage coil with a 5-cm outer diameter. After the acquisition of scout images, six to eight coronal plane images were taken from between 3 mm behind the olfactory bulb and the caudal portion of the cerebellum. Each slice was 2 mm thick without any gaps, matrix size 320×160 and an 8×4 cm field of view. T2-weighted fast spin echo (FSE) sequences were optimized to detect the lesion size. The acquisition parameters were: TE/TR 105/4000 ms, echo train length 53, NEX 8. Each image was determined by a consensus of two observers blinded to the G-CSF/MPBSCs group, G-CSF only group, or control group.

The day 28 photos of anatomy, fluorescence, and MRI of the rats were obtained. It was found that the rats in the CSF/MPBSC group had significantly smaller infarcted areas than those in the other two groups.

To verify the local neuronal metabolism, Proton Magnetic Resonance Spectroscopy ($^1$H-MRS) was used to assess the neuronal activity of each rat at day 3, 7, 14 and 28 after the treatments. $^1$H-MRS was performed using the MRI scanner noted above with a multi-voxel technique. T2-weighted transverse, coronal, or sagittal images were used to localize the volume of interest (VOI). The VOI (0.5×0.5×0.5 cm) was precisely localized centrally to the infarcted brain using two or three images (transverse and sagittal/coronal). The spectroscopic acquisition parameters were as follows: TR=3.0 sec/TE=30 msec and NS=36 AVG with Proton Brain Exam (PROBE) (GE Medical Systems). CHESS (CHEmical Shift Selective) sequence was used for suppression of the $H_2O$ signal. All raw data were transferred to a Sun Sparc-10 workstation (SUN Computer Inc., Sunnyvale, Calif.), and processed using Spectral Analysis/General Electric (SA/GE) software (GE Medical Systems) incorporating low frequency filtering of residual water signals, apodization by 0.5 Hz of exponential line broadening, zerofilling of 8 k, Fourier transformation, and lorenzian to gaussian transformation according to the scheme in the manner described in Kreis et al., Radiology. 1992; 182(1):19-27. Metabolic peaks were fitted by the lorenzian line shape at known frequencies of N-acetylaspartate (NAA) at 2.02 ppm, creatine (Cr) at 3.03 ppm, choline and cholinecontaining compounds (Cho) at 3.22 ppm. The values of the [NAA/Cr] and [NAA/Cho] ratios were calculated. The result of the metabolic ratio is presented as mean±SE.

In an ischemia-free normal rats, the cerebral cortex $^1$H-MRS displayed three signals: choline (Cho), creatine (Cr) and N-acetyl-aspartate (NAA) (Lu et al., 1997, Magn. Reson. Med.; 37(1):18-23.). The $^1$H-MRS of infracted brains (using a multi-voxel technique) showed a sharp decrease in NAA signaling together with a mild decrease in Cho and Cr signals.

Four weeks after the treatments, significant improvements in neuronal activity were observed in the rats in the G-CSF/MPBSC group. More specifically, they showed improved NAA/Cho and NAA/Cr ratios (2.77±0.13 and 2.95±0.13, respectively) (n=6). In contrast, the NAA/Cho and NAA/Cr ratios were 1.72±0.11 and 1.97±0.15; 1.69±0.13 and 1.88±0.17, respectively (n=6) for the rats in the G-CSF and Control group.

Bromodeoxyuridine (BrdU; Sigma Chemical, MO) labeling was conducted according to the method described in Zhang, et al. (Neuroscience. 2001; 105(1):33-41) to determine whether mobilized stem cells homed and engrafted into the brain following ischemia. More specifically, the above-described rats were anesthetized with chloral hydrate (0.4 g/kg, ip) and their brains fixed by transcardial perfusion with saline, followed by perfusion and immersion in 4% paraformaldehyde and embedded in 30% sucrose. A series of adjacent 20-µm-thick sections were cut from each brain in the coronal plane, stained with H&E, and observed by light microscopy (Nikon, E600). For BrdU immunostaining, DNA was first denatured by incubating each section in 50% formamide of 2× standard saline citrate at 65° C. for 2 hours, then in 2 N HCl at 37° C. for 30 minutes, and finally rinsed in 0.1 M boric acid with pH 8.5. Sections were then rinsed with Tris buffer and treated with 1% $H_2O_2$ to block endogenous peroxidase. The immunostaining procedure was performed using the labeled streptavidin-biotin (LSAB) method (DAKO LASB-2 Kit, Peroxidase, DAKO). Brain tissue, on a silane-coated slide, was placed in a boiling citrate buffer (pH 6, ChemMate, DAKO) twice for 5 minutes in a microwave oven at 750 W, after deparaffinization and rehydration. Tissues were then incubated with the appropriate diluted primary antibodies to BrdU (1:400, Mannheim, Germany; or 1:200, Sigma), at room temperature for 1 hour. After washing with Tris-buffered saline, containing 0.1% Tween-20 (TBS-T), the specimens were sequentially incubated for 10 to 30 min with biotinylated anti-rabbit and anti-mouse (1:200, R&D Systems) immunoglobulins and peroxidase-labeled streptavidin. Staining was performed after a 10-minute incubation with a freshly prepared substrate-chromogen solution, containing 3% 3-amino-9-ethylcarbazole and hydrogen peroxide. Finally, the slides were lightly counterstained with hematoxylin, washed with water, and then mounted. Negative control sections were stained with identical preparations of brain tissue specimen, except that primary antibodies were omitted. Quantification of BrdU immunoreactive cells was counted digitally using a 60× objective lens (Carl Zeiss LSM510) via a computer imaging analysis system (Imaging Research, Canada).

It was found that BrdU immunoreactive cells were detected mainly in the penumbra area, striatum, and subventricular area of the lateral ventricle of the rats in the G-CSF/MPBSC group or G-CSF group. Cumulative labeling of BrdU, revealed a few BrdU immunoreactive cells in the ipsilateral hemisphere near the penumbra area, the striatal region, and the subventricular region in the G-CSF/MPBSC and the G-CSF groups. BrdU immunoreactive cells were also found around the lumen of varying calibers of blood vessels (and also in the vessel walls of endothelial cells), suggesting that mobilized stem cells may participate in angiogenesis. In BrdU pulse labeling experiments, the number of BrdU immunoreactive cells significantly increased in the G-CSF/MPBSC treated rats (about 1750; n=8) compared with those treated with G-CSF only (about 800; n=7) and saline control rats (about 600; n=8). These results indicate that G-CSF/MPBSC stimulated stem cell mobilization, homing, and engraftment into the brain following cerebral ischemia.

Immunofluorescent staining were conducted to determine whether mobilized and/or transplanted MPBSCs could differentiate into neurons, glial cells, or endothelial cells in ischemic brains. Confocal microscopy was carried out to identify whether cell type-specific markers co-localized with exogenous transplanted MPBSCs (bisbenzimide-labeled) and endogenous homing stem cells (BrdU immunoreactive). Each coronal section was incubated with cell type-specific antibodies: glial fibrillary acidic protein ("GFAP," for astrocyte, 1:400, Sigma), Von-Willebrand factor ("vWF," for endothelial cell, 1:400, Sigma), neuronal nuclear antigen ("Neu-N," for neuronal nuclei, 1:200, Chemicon), microtubule-associated protein 2 ("MAP-2," for neuronal dendrites, 1:200; BM), CXCR4 (CD 184, 1:100, Torrey Pines Biolab), or Doublecortin ("Dcx," 1:100, Santa Cruz Biotechnology) with Cy3 (Jackson Immunoresearch PA USA, 1:500) staining.

The results showed that some bis-benzimide labeled cells (blue, cell nuclei-fluoresce spontaneously) colocalized with antibodies against MAP-2, Nestin, Neu-N and GFAP (red, neural cell-type specific markers) in the penumbra of G-CSF/MPBSC-treated ischemic rat brains. Percentages of bisbenzimide-labeled cells colocalizing with specific markers MAP-2, Nestin, Neu-N, and GFAP were about 3%, 3%, 2%, 5%, respectively. Further, in the colocalized study of the endogenous (homing) stem cells, the result showed some BrdU$^+$ cells colocalized with markers for MAP-2 or GFAP. These findings indicate that the G-CSF/MPBSC treatment enhanced mobilized stem cell homing and neurogenesis, thereby generating new neural tissue to repair injured areas of the brain.

To determine whether the G-CSF/MPBSCs treatment leads to angiogenesis, three approaches were used on brain slices from the rats in the G-CSF/MPBSC, G-CSF, and Control groups. The three approaches were double immunofluorescent staining, FITC-dextran perfusion studies, and blood vessel density assays.

An immunofluorescent staining was conduced in the manner described above. The results indicate that several exogenous transplanted MPBSCs (bisbenzimide-labeled) and endogenous homing HSCs (BrdU immunoreactive) showed vascular phenotypes (vWF+) around the perivascular and endothelial regions of the ischemic hemispheres of G-CSF/MPBSC treated rats.

Cerebral microcirculation was preformed by administering a fluorescent plasma marker (FITC-dextran, Sigma) intravenously to the rats and observing them under fluorescent microscopy (Carl Zeiss, Axiovert 200M) according to the method described in Morris et al. (Brain Res. Protoc. 1999; 4:185-191). Visual inspection indicated that treatment with G-CSF/MPBSCs (n=6) significantly enhanced cerebral microvascular perfusion with FITC-dextran in comparison with G-CSF only or control (n=6).

To quantify the cerebral blood vessel density, each rat was anesthetized with chloral hydrate and perfused with 4% paraformaldehyde. Histological sections (6 µm) were stained according to the Trichrome-Masson procedure (Bio-Optica, Milan, Italy) and the number of blood vessels determined in the manner described in Facchiano et al. (Am. J. Pathol. 2002; 161(2):531-541). Quantitative measurement of blood vessel density was examined by the Trichrome-Masson's procedure. The results showed that ischemic rats treated with G-CSF/MPBSCs (n=4) showed significantly more neovasculature in the penumbric area (about 300 vessels/mm$^2$) than the rats in the G-CSF group (100 vessels/mm²) or the control group (about 130 vessels/mm²; n=4).

The results described above indicate that G-CSF/MPBSC transplantation induced angiogenesis in vivo.

It is known that vascular remodeling in local neo-vasculization involves perivascular infiltration of stem cells-derived macrophage/microglial (MA/MI) and increased expression of β1-integrin (Heil et al., 2002, Am. J. Physiol. Heart Circ Physiol, 283(6):H2411-2419. To examine the association between angiogenesis and macrophage, brain sections (6 μm) of the G-CSF/MPBSCs treated rats were examined by double immunofluorescent staining and FITC-dextran perfusion in the manner described in Morris et al., 1999, Brain Res. Brain Res. Protoc. 4(2):185-191. To quantify the cerebral blood vessel density and examine the vascular remodeling by macrophage, the rats were anesthetized with chloral hydrate and perfused with 4% paraformaldehyde. The sections were stained with specific antibody to α-SMA (1:100, Sigma), OX-42 (1:400, Serotec), ED-1 (1:500, Acris) and conjugated with Cy-3 (1:500, Jackson Immunoresearch PA USA). The number of blood vessels was determined according to the method described in Tanaka et al., 2003, Circ Res. 93(8):783-790. The total number of positive MA/MI per section was counted by the method described in Pipp et al., 2003, Circ Res. 92(4):378-385.

The results indicate that several exogenous transplanted MPBSCs (bisbenzimide-labeled) exhibited macrophage/microglia (MA/MI) phenotypes (OX-42 cells) infiltrating around the perivascular regions (FITC-dextran perfused vessels) of the ischemic hemispheres of G-CSF/MPBSC treated rats. Significantly more MA/MI were observed around the vessels in the G-CSF/MPBSCs-treated rats than in G-CSF only treated rats and control rats.

To check the expression of β1-integrin, brain tissue samples were subjected to Western blot assays using a specific anti-β1-integrin antibody (Chemicon). Moreover, β1-integrin activation was blocked by cyclic RGD peptides (1 μg/ml, Chemicon), which had been added to the MPBSCs and injected into the ischemic brain. Finally, neurological behavioral measurement as described above was examined to evaluate the treatments of G-CSF/MPBSCs with cyclic RGD peptides, G-CSF only, and control.

It was found that β1-integrin protein was expressed at a significantly higher level in the G-CSF/MPBSCs-treated rats (n=4) than in rats treated with G-CSF only (n=4) and control rats (n=4). In the presence of cyclic RGD peptides, neither the expression of β1-integrin nor the neurological behavior measurement showed significant difference among the three groups. These results suggest that cyclic RGD peptides inhibited the expression of β1-integrin and that β1-integrin was essential to the neurological behavior improvement shown in the CSF/MPBSCs treated rats.

Increased vessel density would enhance neuronal survival, especially associated with an increased cerebral blood flow (CBF), which would result in efficient delivery of oxygen and neutrients. Therefore, in order to examine the CBF in the ischemic brain, the treated rats were injected with diamox and monitored by laser doppler flowmetry (LDF) under anesthesia after cerebral ischemia. More specifically, each of the rats was positioned in a stereotaxic frame. Baseline local cortical blood flow (bCBF) was measured continuously with a laser doppler flowmeter (LDF monitor, Moore Instrument England) in an anesthetized state (chloral hydrate) according to the method described in Demolis et al., Stroke, 2000; 31(2):508-515. The reactive cerebral blood flow (rCBF) was examined after intraperitoneal injection of 50 mg/kg acetazolamide (Diamox, Lederle) and defined as percentage changes of bCBF. The results show a significant increase in rCBF of the middle cerebral artery cortex of the ischemic brain in the rats of the G-CSF/MPBSC group (about 100%, 130%, 160%, 200%, and 185% at days 1, 7, 14, 21, and 28, respectively) compared with those in the G-CSF group (about 100%, 105%, 110%, 120%, and 115%, respectively) or in the control group (about 100%, 105%, 110%, 110%, and 110%, respectively). They suggest that G-CSF/MPBSC treatment facilitated reactive cerebral blood flow in the ischemic brain.

Quantitative RT-PCR was performed to examine in vivo synthesis of various neurotrophic factors that were known to neuroprotect the ischemic cortical area. These neurotrophic factors include SDF-1, BDNF, GDNF, NGF, TGF-β, FGF-II and VEGF. PCR primers specific for these factor are summarized in the table below:

| Factor | PCR Primer Sequences | SEQ ID NO: | PCR fragment |
| --- | --- | --- | --- |
| SDF-1 | sense-TTGCCAGCACAAAGACACTCC | 1 | 243 bp |
|  | anti-sense-CTCCAAAGCAAACCGAATACAG | 2 |  |
| BDNF | sense-CAGTGGACATGTCCGGTGGGACGGTC | 3 | 533 bp |
|  | anti-sense-TTCTTGGCAACGGCAACAAACCACAAC | 4 |  |
| GDNF | sense-CCACACCGTTTAGCGGAATGC | 5 | 638 bp |
|  | anti-sense-CGGGACTCTAAGATGAAGTTATGGG | 6 |  |
| NGF | sense-GTTTTGGCCAGTGGTCGTGCAG | 7 | 498 bp |
|  | anti-sense-CCGCTTGCTCCTGTGAGTCCTG | 8 |  |
| TGF-β | sense-CCGCCTCCCCCATGCCGCCC | 9 | 710 bp |
|  | anti-sense-CGGGGCGGGGCTTCAGCTGC | 10 |  |

-continued

| Factor | PCR Primer Sequences | SEQ ID NO: | PCR fragment |
|---|---|---|---|
| FGF-II | sense-TCACTTCGCTTCCCGCACTG | 11 | 252 bp |
| | anti-sense-GCCGTCCATCTTCCTTCATA | 12 | |
| VEGF | sense-GCTCTCTTGGGTGCACTGGA | 13 | 431 bp |
| | anti-sense-CACCGCCTTGGCTTGTCACA | 14 | |

More specifically, the rats in the G-CSF/MPBSC group (n=5), the G-CSF group (n=5) and the Control group (n=5) were anesthetized with chloral hydrate (0.4 g/kg, ip) at days 3, 7, 14, and 28 after initiation of treatments. Ischemic cortical and striatal areas were dissected out on ice immediately. Subsequently, brain tissue samples were homogenized by a plastic hemogenizer and total RNA was isolated using the RNeasy® (Qiagen). The relative amount of target mRNA was determined by quantitative RT-PCR (QRT-PCR) using SYBR Green following manufacturer's instructions (Roche Diagnostics). The relative expression levels of target mRNAs were normalized against GAPDH as an internal standard. QRT-PCR was performed using the ABI Prism 7900 Sequence Detection System (Applied Biosystem) according to a method modified from that described in Luo et al., Respir. Res. 2004; 5(1):20. The conventional RT-PCR was performed according to the method described in Shyu et al. (Cell Mol. Neurobiol. 2004; 24(2):257-268). The results revealed significantly increased expression of SDF-1, VEGF, GDNF and BDNF in ischemic rats treated with G-CSF/MPBSCs in comparison with the G-CSF only group and vehicle control group. In QRT-PCR analysis, the ratio of expression level of SDF-1, VEGF, and BDNF to GAPDH peaked at about a 2-fold increase in G-CSF/MPBSCs compared with that of rats in the G-CSF only group or control group.

The above-described results indicate that rats receiving G-CSF intracerebral MPBSC transplantation showed significantly improved neurological function following chronic cerebral ischemia in comparison with G-CSF-only-treated rats and vehicle-treated control rats. In the G-CSF/MPBSC group, exogenous transplanted MPBSCs and endogenous homing stem cells were seen to migrate toward the cerebral infarcted zone and differentiate into glial cells (GFAP$^+$), neurons (Nestin$^+$, MAP-2$^+$ and Neu-N$^+$) and vascular endothelial cells (vWF$^+$), thereby enhancing neuroplasticty in the ischemic brain. Evidence of stem cell homing and migration was also demonstrated by the immunofluorescent study of specific markers for CXCR4 and Dcx. In addition, cortical neuronal activity as evaluated by Proton MR spectroscopy ($^1$H-MRS) increased considerably in rats of the G-CSF/MPBSC in comparison with those of the G-CSF or Control group. In addition, the G-CSF/MPBSC treatment promoted the formation of new vessels and increased the local cortical blood flow in the ischemic hemisphere. Finally, the rats in the G-CSF/MPBSC group also exhibited a significant increase in modulation of neurotrophic factor expression in the ischemic hemisphere.

It has been known that G-CSF augmented choline acetyltransferase activity in mouse embryonic primary septal neurons and promote survival of septal cholinergic neurons in adult rats (Konishi et al., Brain Res. 1993; 609(1-2):29-35.). G-CSF not only protects cerebellar granular neurons against glutamate toxicity through STAT3 signaling, but also diminishes the infarct size in an "acute" cerebral ischemic animal model (Schabitz et al., Stroke. 2003; 34(3):745-751). It has been demonstrated that functional recovery of "acute" stroke rats is through the mechanism of G-CSF-stimulated stem cell homing to the penumbric region, thereby repairing the ischemic brain (Shyu et al., Circulation. 2004; 110(13):1847-1854.). In this invention, it was shown that, in a chronic stroke animal model, subcutaneous injection of G-CSF only did not significantly improve neurological function in comparison with control rats. G-CSF treatment increased mobilization of PBSCs to "acute" damaged areas of the brain, and this increase might in turn stimulate cell division around the injured region. Further, it is possible that interaction of PBSCs with injured brain tissue leads PBSCs or parenchymal cells to produce trophic factors that may contribute to the recovery of neural functions. Although G-CSF exhibited a strong neuroprotective effect in rescuing ischemic neurons in this study, extensively diminished numbers of mobilized PBSCs through G-CSF induced homing to the "chronic" ischemic brain region seems to be the major reason for the poor recovery of neurological dysfunction in rats receiving chronic cerebral ischemia.

It has been indicated that SDF-1/CXCR4 is a strong chemo-attractant for CD34$^+$ cells and plays an important role in HSC trafficking between peripheral circulation and bone marrow (Petit et al., Nat. Immunol. 2002; 3(7):687-694)) and that focal cerebral ischemia causes an increase in SDF-1/CXCR4 expression in regions adjacent to the infarcted area (Hill et al., J. Neuropathol. Exp. Neurol. 2004; 63(1):84-96). This lesion-induced up-regulation of endothelial SDF-1 and the appearance of increased CXCR4 expression in the ischemic hemisphere four hours after ischemia indicate that cerebro-endothelial SDF-1 could be a chemo-attractant for peripheral blood cells. However, the upregulation of SDF-1 in the penumbric area showed to diminish significantly 7 days after the induction of cerebral ischemia. In the "chronic" stroke model described therein, the expression of SDF-1 may have decreased progressively in comparison with "acute" ischemic brain. Therefore, it could be that decreased expression of SDF-1 one week after cerebral ischemia may not result in enough stem cells homing to the ischemic brain, which may result in the poor recovery of post-ischemic neurological performance after G-CSF treatment seen in this study.

In this study, a novel therapeutic strategy was developed to treat a subject having chronic stroke using subcutaneous injection of G-CSF in combination with intracerebral MPBSC transplantation. Neurological dysfunction after chronic stroke showed significant improvement in the rats in the G-CSF/MPBSC group as compared with those in the G-CSF or Control group. Exogenous MPBSC transplantation was found to increase the number of endogenously mobilized stem cells homing to the lesioned brain resulting in a significant improvement in neurological function after chronic stroke. Furthermore, exogenous MPBSCs transplanted into the ischemic hemisphere resulted in significant increases in neurotrophic factors including SDF-1 and BDNG in G-CSF i MPBSC treated rats compared to the G-CSF only and control treated rats. These trophic factors not only increased the survival rats of the ischemic neurons in the penumbra region, but also induced endogenously mobilized HSCs to migrate and home to the ishemic brain to repair it. Specifically, one of these factors, SDF-1, may be the key substance that induced endogenous stem cell targeting to the ischemic hemisphere. Stumm et al. demonstrated that focal cerebral ischemia causes an increase in SDF-1 expression in regions adjacent to the infarcted area (Stumm et al., J. Neurosci. 2002; 22(14): 5865-5878). SDF-1 is a CXC chemokine constitutively produced by bone marrow stromal cells and is a potent chemoattractant for stem cells. By attracting endogenous stem cells to the ischemic region, a SDF-1/CXCR4 interaction may be directly involved in vascular remodeling, angiogenesis and neurogenesis, thereby alleviating stroke symptoms. As a consequence of this autocrine regulatory pathway, endothelial and neuronal progenitor cells may mobilize and fuse with each other, a step required for subsequent formation of a structured network of branching vessels and neurons (Chen et al., Circ. Res. 2003; 92(6):692-699).

In this study, transplanted MPBSCs and endogenous homing HSCs were all $CD34^+$. $CD34^+$ cells have been proven to enhance neovascularization in the penumbra region of ischemic brain and subsequently promote prominent neurogenesis (Taguchi et al., J. Clin. Invest. 2004; 114(3):330-338). A relationship between angiogenesis and neurogenesis induced by $CD34^+$ cells would be consistent with regeneration of parenchymal cells after injury in other organs (Toda et al., J. Pathol. 1999; 188(4):415-422; and Ross et al., Hepatology. 2001; 34(6):1135-1148.). Thus, the mechanism underlying this observation of co-existence of neurogenesis and angiogenesis might include enhanced production of trophic factors such as BDNF and PDGF by $CD34^+$ cell-derived neovasculatures and directly result in differentiation of these $CD34^+$ stem cells into neuron/glial cells. Furthermore, $CD34^+$ cell-derived neovasculatures contributing to maintaining newly formed neuron/glial cells have been shown to integrate into networks in adult animals and provide an environment conducive to neurogenesis.

EXAMPLE 2

G-CSF's neuroprotection role on dopaminergic (DA) neurons was examined. For this purpose, rat ventral mesencephalic neuron-glia primary cultures were prepared following a method modified from that described in Liu B, J. Pharmcol. Exp. Ther. 2000; 293: 607-617. Briefly, fresh ventral mesencephalic tissues were dissected from embryonic day 13/14 Fischer 344 rats and disaggregated by trituration in the presence of 10 mg/mL trypsin and 5 mg/ml DNase. Cells were seeded into poly-D-lysine-precoated 24-well plates and maintained at a density of 200,000 cells per well in minimum essential medium (MEM, GIBCO-BRL) supplemented with 10% heat-inactivated fetal bovin serum (FBS) and 10% heat-inactivated horse serum (HS), 1 g/l glucose, 2 mM L-glutamate, 1 mM sodium pyruvate, 100 μM nonessential amino acids, 50 IU/mL penicillin, and 50 μg/ml streptomycin. The cellular composition of the culture was determined by immunocytochemistry. It was found that the culture contained about 11% OX-42 immunoreactive (IR) microglia, 48% GFAP-IR astrocytes and 40% Neu-N-IR neurons (of which 2-2.5% were DA neurons). The cultures were replenished with 0.5 ml/well fresh medium at day 3. At day 7, the cells were incubated with a MEM medium containing different concentrations of G-CSF (Filgrastim, Kirin, Japan; 0, 0.001, 0.01, 0.1 and 1 μg/ml). The MEM medium contained 2% FBS, 2% HS, 2 mM L-glutamine, 1 mM sodium pyruvate, 50 U/ml penicillin, and 50 μg/ml streptomycin. Two hours later, the cells were incubated with MPTP (MPP+, 70 μM, 1 ml/well; Sigma, St Louis) or a control vehicle. MPTP is known to be toxic to DA neurons.

Forty-eight hours later, immunostaining was performed according to the method described in Kim J. Neurosci. 2000; 20: 6309-6316. Briefly, cells were fixed with 4% paraformaldehyde, followed by blocking with PBS containing 0.4% Triton X-100, 1% bovine serum albumin, and 4% serum. After this blocking, the cells were incubated with primary antibodies at 4° C. overnight. DA neurons were revealed by antibodies against Neu-N (1:200, Chemicon), MAP-2 (1:200; BM), and tyrosine hydroxylase ("TH," specific for dopaminergic neuron, 1:200; Santa Cruis). Glial cells were recognized by anti-GFAP antibody (1:400, Sigma). The cells were then incubated for 10-30 minutes with biotinylated anti-rabbit and anti-mouse immunoglobulins and peroxidase-labeled streptavidine. The staining was visualized by a freshly prepared substrate-chromogen solution (Diaminobenzidene, S7101-8) for 10-minutes. Finally, the slides were lightly counterstained with hematoxylin, washed with water, and mounted. The extent of cell immunoreactivity was measured as the number of cells per 10 HPFs (at least 20 fields were counted).

The density of DA neuron and pattern of neurite outgrowth was analyzed in the manner described in Oh et al. (Neurosci. Lett, 1996; 202: 161-164). Briefly, morphological characteristics were quantified in ten randomly selected fields under a light microscope (Carl Zeiss, Axioskop 2 plus, Germany). A neurite was defined as a process arising from the soma. The length of the primary neurite was defined as the distance from the soma to the tip of the longest branch. The number of neurites per cell was the identified. Only those processes that were longer than two times of one cell diameter were counted.

As expected, MPTP induced DA neuron death. However, in the presence G-CSF, TH immunoreactive (TH-IR) neurons displayed more extensive outgrowth of neurites compared to control cells. Also, the number of TH-IR neurons increased significantly in a G-CSF dose-dependent manner. More specifically, in presence of MPTP alone, the number of TH-IR decreased to about 32% of control level (100%). In contrast, in presence of 0.01, 0.1, 1.0, and 10 μg/ml of G-CSF, the numbers recovered to about 48%, 56%, 72%, and 90%, respectively. These results indicate that G-CSF protected DA neurons from MPTP-induced neurotoxicity.

The just-described experiments were repeated except that no MPTP was added to the cell culture. It was found that, in the presence of different concentrations of G-CSF, TH-IR neurons displayed more extensive neurites outgrowth and the number of TH-IR neurons increased significantly. Here, 0.001, 0.01, 0.1 and 1 μg/ml of G-CSF respectively resulted in increases by about 25%, 33%, 80%, and 40%. These results suggest that CSF itself also promoted DA neurons.

In order to determine the mechanism of G-CSF neuronal protection, primary neuron-glial cell cultures were treated with G-CSF and the expression of neurotrophic factors were identified by RT-PCR using specific primers listed in the table below:

| Factor | PCR Primer Sequence | SEQ ID NO: | PCR Fragment |
|---|---|---|---|
| SDF-1 | sense-TTGCCAGCACAAAGACACTCC | 1 | 243 bp |
|  | anti-sense-CTCCAAAGCAAACCGAATACAG | 2 |  |
| BDNF | sense-CAGTGGACATGTCCGGTGGGACGGTC | 3 | 533 bp |
|  | anti-sense-TTCTTGGCAACGGCAACAAACCACAAC | 4 |  |
| GDNF | sense-CCACACCGTTTAGCGGAATGC | 5 | 638 bp |
|  | anti-sense-CGGGACTCTAAGATGAAGTTATGGG | 6 |  |
| NGF | sense-GTTTTGGCCAGTGGTCGTGCAG | 7 | 498 bp |
|  | anti-sense-CCGCTTGCTCCTGTGAGTCCTG | 8 |  |
| TGF-β | sense-CCGCCTCCCCCATGCCGCCC | 9 | 710 bp |
|  | anti-sense-CGGGGCGGGGCTTCAGCTGC | 10 |  |
| FGF-II | sense-TCACTTCGCTTCCCGCACTG | 11 | 252 bp |
|  | anti-sense-GCCGTCCATCTTCCTTCATA | 12 |  |
| VEGF | sense-GCTCTCTTGGGTGCACTGGA | 13 | 431 bp |
|  | anti-sense-CACCGCCTTGGCTTGTCACA | 14 |  |

Primary neuron-glial culture was treated with G-CSF of different concentration and MPTP (MPP+, 70 μM) for 24 hours in the same manner described above. RNA was extracted by an RNA-extraction kit (Qiagen, USA), according to the manufacturer's instructions. A total of 5 μg RNA was transcribed with Superscript II reverse transcriptase and oligo-dT (Invitrogen, USA). cDNA samples were subjected to PCR amplification (Cetus Thermocycler, Perkin Elmer) with specific primers under linear conditions. The cycling parameters were as follows: denaturation at 94° C. for 30 seconds, annealing at 55° C. to 61° C. (depending on the primer) for 30 seconds, and elongation at 72° C. for 1 minute (30 cycles). GAPDH was used as an internal control for the RT-PCR. The sense primer for GADPH was 5'-GGCTGTGT-GTCCCTGTAT-3' (SEQ ID NO:15) and the anti-sense primer 5'-CCGCTCATTGCCGATAGTG-3' (SEQ ID NO:16). The PCR products were visualized by electrophoresis in a 3% agarose gel, and stained with 0.5 μg/ml ethidium bromide. Products of each gene were verified by their predicted size. Quantification of band intensity was performed by densitometric analysis (Digital Image Analysis System, PDI, Huntington Station, NY, USA), and calculated as the optical density×area of band.

It was found that treatment of G-CSF and MPTP led to significantly increased mRNA expression of SDF-1, GDNF, BDNF and NGF in a G-CSF dose-dependent manner in comparison to the control (without G-CSF and MPTP treatment). The ratio of SDF-1, BDNF and GDNF to GAPDH, summarized below in the table below, peaked at about a 2-fold increase in comparison to the control.

| G-CSF | MPTP (μM) | Ratio of Neurotrophic Factor level to GAPDH level | | | |
|---|---|---|---|---|---|
|  |  | BDNF | SDF-1 | GDNF | NGF |
| Base | 0 | 1.00 | 1.00 | 1.00 | 1.00 |
| 0.00 | 70 | ~0.90 | ~1.20 | ~1.20 | ~1.30 |
| 0.01 | 70 | ~1.50 | ~1.30 | ~1.40 | ~1.40 |
| 0.10 | 70 | ~2.10 | ~1.50 | ~2.10 | ~2.10 |
| 1.00 | 70 | ~1.40 | ~2.00 | ~1.40 | ~1.00 |
| 10.00 | 70 | ~1.20 | ~1.20 | ~1.10 | ~1.20 |

The results suggest that G-CSF itself significantly upregulates the expression of neurotrophic factors including BDNF, GDNF and SDF-1, which might in turn protect DA neurons from MPTP-induced neurotoxicity.

EXAMPLE 3

An animal model of Parkinson's disease was used to evaluate the effects of G-CSF. Adult male Sprague-Dawley rats (weighing 250-300 g) were used in this study. In each rat, the dopamine-innervated striata were unilaterally lesioned by injections of 6-hydroxydopamine (6-OHDA, Sigma, St Louis) into the right median forebrain bundle as determined from the bregma and the surface of the skull according to the method described in Costantini (Eur. J. Neurosci. 2001; 13: 1085-1092). Each rat received 6 μg of 6-OHDA dissolved in 6 μl of physiological saline containing 0.02% ascorbic acid. The solution was infused at a rate of approximately 0.5 μl/minute using a 22-gauge 10-μl microsyringe (MS-NI Ito Microsyringe; Shizuoka, Japan), with the microsyringe left in position for an additional 5 minutes before retraction. Amphetamine-induced rotational behavior was assessed at 2, 4, 6, and 8 weeks after 6-OHDA injection.

A rotameter trial was used to assess rotational behavior before and after 6-OHDA lesioning. The behavioral measurement scores were normalized by the respective baseline scores. Since 6-OHDA lesioning causes imbalanced motor activity, all of the experimental rats developed significant rotation and turned ipsilateral to the side of the lesion on day 7 following amphetamine injection. In brief, the rats were placed in individual plastic hemispheric bowls (Rotamter, Columbus Instruments, Ohio, USA) and allowed to habituate for 10 minutes before being injected with an intraperitoneal dose of amphetamine (4 mg/kg, i.p.). Rotational behavior was monitored by a computerized activity monitor system for one hour in a closed room to avoid any environmental disturbance. Rats turning ipsi-lateral toward the lesioned side (clockwise) at a rate of seven or more rotations per minute were selected as Parkinsonian models. Rats reaching seven turns per minutes exhibited a greater than 97% reduction in striatal dopamine levels and showed a permanent hemi-parkinsonian syndrome (Schmidt R H, Acta Physiol. Scand. Suppl. 1983; 522: 19-28). All procedures were in accordance with our University Institutional guidelines. The whole procedure was well tolerated as all tested animals survived the experimental protocol.

Three weeks later, thirty of the model rats were divided into three groups (10 in each), i.e., "G-CSF alone," "G-CSF/PBSC," and "control" groups. The rats in the control group were injected with saline. The rats in the other two groups were injected subcutaneously with human recombinant G-CSF (50 μg/kg) once a day for 5 days (Bodine D M, Blood 1994; 84: 1482-1491). Then, the rats in the G-CSF/PBSC group were injected intracerebrally with PBSCs ($1 \times 10^5$ PBSCs in 3-5 µl of PBS) in the same manner described in Example 1 above. The PBSCs had been purified in the same manner described in Example 1 above.

The above-described rotameter trial was conducted again. It was found that rats administered with G-CSF alone and G-CSF/PBSCs exhibited recovery over time from amphetamine-induced turning behavior compared with that of controls. In particular, rats receiving G-CSF together with PBSC transplantation showed a significantly decreased rotational score in comparison to G-CSF alone and control rats respectively at 7 weeks (301±82.8 vs. 750±82.5 and 890±88.9 rotation, *P<0.05), 9 weeks (222±76.5 vs. 710±74.9 and 820±91.7 rotation, *P<0.05) and 11 weeks (133±68.5 vs. 600±91 and 751±93 rotation, **P<0.01) after 6-OHDA lesioning.

To determine whether mobilized stem cells and transplanted PBSCs homed in on the 6-OHDA lesioned brain, BrdU labeling was conducted in the same manner described above in Example 1. Briefly, a cumulative labeling method was used to examine the population of proliferative cells 56 days after 6-OHDA lesioning. Rats received daily injections of BrdU (50 mg/kg, ip.) starting the day after 6-OHDA lesioning. It was found that BrdU immunoreactive cells were detected mainly in the striatum and subventricular area of the lateral ventricle in G-CSF treated rats. Quantification results showed that BrdU-positive cell densities were about 500, 750, and 1380 BrdU-positive cells/mm$^2$ for the control, G-CSF, and G-CSF/PBSC groups, respectively. Cumulative labeling of BrdU, revealed a few BrdU immunoreactive cells in the ipsilateral hemisphere near the substantia niagra and subventricular region. BrdU immunoreactive cells were also found around the lumen of varying calibers of blood vessels in the perivascular portion (also in the vessel wall of endothelial cells), suggesting that the mobilized stem cells participate in angiogenesis.

Double staining immunohistochemistry was performed to determine whether mobilizing HSCs differentiated into neuron, glial, or endothelial cells at ischemic sites in the brains of G-CSF treated rats.

Briefly, each rat was anesthetized with chloral hydrate (0.4 g/kg, ip) and their brains fixed by transcardial perfusion with saline, followed by perfusion and immersion in 4% paraformaldehyde, before being removed and embedded in 30% sucrose. A series of adjacent 20-µm-thick sections were cut from each brain in the coronal plane, stained with H&E and observed by light microscopy (Nikon, E600). For BrdU and TH immunostaining, DNA was first denatured by incubating each section in 50% formamide of 2× standard saline citrate at 65° C. for 2 hours, then in 2 N HCl at 37° C. for 30 minutes, and finally rinsed in 0.1 M boric acid with pH 8.5. Sections were then rinsed with a Tris buffer and treated with 1% $H_2O_2$ to block endogenous peroxidase. The immunostaining procedure was performed using the labeled streptavidin-biotin (LSAB) method (DAKO LASB-2 Kit, Peroxidase, DAKO). Tissue, on a silane-coated slide, was placed in a boiling citrate buffer (pH 6, ChemMate, DAKO) twice for 5 minutes in a microwave oven at 750 W, after deparaffinization and rehydration. Tissues were then incubated with the appropriate diluted primary antibodies to BrdU, TH, and OX-42 (specific for CR3-microglia/macrophages, dilution 1:500, Accurate Chemical) at room temperature for 1 hour. After washing with Tris-buffered saline containing 0.1% Tween-20 (TBS-T), the specimens were sequentially incubated for 10 to 30 min with biotinylated anti-rabbit and anti-mouse (1:200, R&D Systems) immunoglobulins and peroxidase-labeled streptavidin. Staining was performed after a 10-minute incubation with a freshly prepared substrate-chromogen solution, containing 3% 3-amino-9-ethylcarbazole and hydrogen peroxide. Finally, the slides were lightly counterstained with hematoxylin, washed with water, and then mounted. Negative control sections were stained with identical preparations, except that primary antibodies were omitted. Quantification of BrdU, TH and OX-42 immunoreactive cells was performed on paraffin embedded tissue sections. BrdU, TH (substantia niagra-pars compacta, SNpc) and OX-42 immunoreactive cells were counted digitally using a 60× objective (Carl Zeiss LSM510) via a computer imaging analysis system (Imaging Research, Canada). The striatal density of TH immunoreactivity was determined as described in Wu, J. Neurosci. 2002; 22:1763-1771).

Laser-Scanning confocal microscopy was conducted to identify cell type-specific markers expressed in BrdU$^+$ and bisbenzimide cells. The expression of GFAP, vWF, microtubule-associated protein 2 (MAP-2), neuronal nuclei (Neu-N) and TH were examined in the manner described in Example 1 above.

The results showed that some BrdU signals co-localized with Neu-N, MAP-2, GFAP, vWF, or TH in G-CSF treated rats brains. Ischemic cortical areas of G-CSF treated rats revealed an increase in BrdU$^+$ cells co-expressing the neuronal phenotypes of Neu-N$^+$ and MAP-2$^+$ cells and the glial phenotype of GFAP$^+$ cells compared with saline-treated rats. Some BrdU$^+$ cells, showing vascular phenotypes (vWF$^+$ cells), were found around the perivascular and endothelial regions in the ischemic hemispheres of G-CSF treated rats. These findings indicate that G-CSF induced HSCs and thereby generated new neural and vascular tissue in injured brain areas.

To examine whether G-CSF protects against 6-OHDA induced neurotoxicity to the DA neurons, the number of DA neuron bodies in the SNpc and the fiber density of DA neurons in striatum were determined. It was found that, the number of TH-positive neurons of the rats in the G-CSF/PBSC group (about 7900) were significantly higher than that for the G-CSF (about 3000) or control group (2400). In addition, the rats in the G-CSF/PBSC group showed significant sparing of striatal TH-positive fiber density (OD) (about 0.16) in comparing to those in the G-CSF group (about 0.06) or the control group (about 0.025). These findings indicate that G-CSF/PBSC protected the nigrostriatal pathway against the effect of neurotoxicity induced by 6-OHDA.

The OX-42, a specific marker for microglial activation, was examined to determine whether neuroprotection by G-CSF/PBSC is associated with inhibition of 6-OHDA-induced microglial response. The activation of microglial cells was graded qualitatively (grade I: none, grade II: focal and grade III: widespread activation) in the manner described in Cicchetti (Eur. J. Neurosci. 2002; 15:991-998). Activated microglial cells appeared to be characterized by larger cell bodies, shorter proximal processes, reduced ramification of the distal processes and increased staining intensity of OX-42. In the G-CSF/PBSC (n=10), microglial activation was present as grade I in seven rats (70%) and grade II in three rats (30%). In the G-CSF group (n=10), microglial activation was present as grade II in six rats (60%) and grade III in four rats (30%). In contrast, in the control group, microglial activation was present as grade II in one rat (10%) and grade III in nine rats (90%). These results indicate that G-CSF/PBSC inhibited 6-OHDA-induced microglial activation.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of increasing the expression level of a neurotrophic factor in a cell, comprising contacting the cell with granulocyte-colony stimulating factor, and measuring an expression level of the neurotrophic factor in a sample obtained from the cell or a medium containing the cell after the contacting step to confirm an increase in the expression level, wherein the neurotrophic factor is selected from the group consisting of brain-derived neurotrophic factor, glial-cell line derived neurotrophic factor, nerve growth factor, and stromal cell derived factor-1.

2. The method of claim 1, wherein the neurotrophic factor is brain-derived neurotrophic factor.

3. The method of claim 1, wherein the neurotrophic factor is glial-cell line derived neurotrophic factor.

4. The method of claim 1, wherein the neurotrophic factor is nerve growth factor.

5. The method of claim 1, wherein the neurotrophic factor is stromal cell derived factor-1.

6. The method of claim 1, wherein the cell is in the brain of a subject in need thereof, and the contacting step comprises administering granulocyte-colony stimulating factor to the subject and wherein the sample is obtained from the subject after the administering step to confirm an increase in the expression level.

7. The method of claim 6, wherein the subject is suffering from or being at risk for developing brain tissue damage.

* * * * *

UNITED STATES PATENT AND TRADEMARK OFFICE
CERTIFICATE OF CORRECTION

PATENT NO. : 7,569,545 B2 Page 1 of 1
APPLICATION NO. : 11/134613
DATED : August 4, 2009
INVENTOR(S) : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this

Seventh Day of September, 2010

David J. Kappos
*Director of the United States Patent and Trademark Office*

```
                              SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
ttgccagcac aaagacactc c                                                   21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ctccaaagca aaccgaatac ag                                                  22

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
cagtggacat gtccggtggg acggtc                                              26

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
ttcttggcaa cggcaacaaa ccacaac                                             27

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ccacaccgtt tagcggaatg c                                                   21

<210> SEQ ID NO 6
<211> LENGTH: 25
```

```
<212> TYPE: DNA
<213> ORGANISM: Artificial Sequence
<220> FEATURE:
<223> OTHER INFORMATION: Primer

<400> SEQUENCE: 6
cgggactcta agatgaagtt atggg                                          25

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gttttggcca gtggtcgtgc ag                                             22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccgcttgctc ctgtgagtcc tg                                             22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccgcctcccc catgccgccc                                                20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cggggcgggg cttcagctgc                                                20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tcacttcgct tcccgcactg                                                20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
```

```
                                        -continued
gccgtccatc ttccttcata                                              20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gctctcttgg gtgcactgga                                              20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
caccgccttg gcttgtcaca                                              20

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
ggctgtgtgt ccctgtat                                                18

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
ccgctcattg ccgatagtg                                               19
```